(12) United States Patent
Chen et al.

(10) Patent No.: US 7,534,607 B1
(45) Date of Patent: May 19, 2009

(54) METHOD OF PRODUCING CARDIOMYOCYTES FROM MESENCHYMAL STEM CELLS

(75) Inventors: Wann-Hsin Chen, Hsinchu (TW); Su-Yo Lin, Taipei (TW)

(73) Assignee: Industrial Technology Research Institute, Chutung Town, Hsinchu Hsien (TW)

( * ) Notice: Subject to any disclaimer, the term of this patent is extended or adjusted under 35 U.S.C. 154(b) by 0 days.

(21) Appl. No.: 11/319,113

(22) Filed: Dec. 27, 2005

(51) Int. Cl.
*C12N 5/00* (2006.01)
*C12N 5/02* (2006.01)
*A01N 65/00* (2006.01)

(52) U.S. Cl. ........................ 435/377; 424/93.7
(58) Field of Classification Search .............. None
See application file for complete search history.

(56) References Cited

U.S. PATENT DOCUMENTS

| | | | |
|---|---|---|---|
| 6,387,369 B1 | 5/2002 | Pittenger et al. | |
| 6,491,912 B2 * | 12/2002 | Dinsmore | 424/93.7 |
| 2002/0142457 A1 * | 10/2002 | Umezawa et al. | 435/366 |
| 2003/0031651 A1 * | 2/2003 | Lee et al. | 424/93.7 |
| 2004/0161419 A1 * | 8/2004 | Strom et al. | 424/93.21 |

FOREIGN PATENT DOCUMENTS

| | | |
|---|---|---|
| WO | WO 2004/065589 | 8/2004 |
| WO | WO 2005/056779 | 6/2005 |
| WO | WO 2005/065354 | 7/2005 |

OTHER PUBLICATIONS

Chepda T, Cadau M, Girin P, Frey J, Chamson A. Monitoring of ascorbate at a constant rate in cell culture: effect on cell growth. In Vitro Cell Dev Biol Anim. Jan. 2001;37(1):26-30.*
Heng et al., 2004, Cardiovascular Research, 62: 34-42.*
Takahashi et al., 2003, Circulation, 107: 1912-1916.*
M. Galmiche, V. Koteliansky, J. Briere, P. Herve, and P. Charbord; "Stroma Cells from Human Long-Term Marrow Cultures are Mesenchymal Cells that Differentiate Following a Vascular Smooth Muscle Differentiation Pathway;" Jul. 1993; pp. 66-76.
S. Wakitani, MD., T. Saito, MD., and A. Caplan, PhD.; "Myogenic Cells Derived from Rat Bone Marrow Mesenchymal Stem Cells Exposed to 5-Azacytidine;" Dec. 1995; pp. 1417-1426.
W. Shim, S. Jiang, P. Wong, J. Tan, Y. Chua, Y. Tan, Y. Sin, C. Lim, T. Chua, M. , T. Liu, E. Sim; Ex Vivo Differntiation of Human Adult Bone Marrow Stem Cells into Cardiomyocyte-Like Cells; Jun. 2004; pp. 481-488.
T. Takahashi, MD., B. Lord, BS., P. Schulze, MD., R. Fryer, PhD., S. Sarang, PhD., S. Gullans, PhD., R. Lee, MD.; "Ascorbic Acid Enhances Differentiation of Embryonic Stem Cells into Cardia Myocytes;" Feb. 2003; pp. 1912-1916.
A. Boyum; "Isolation of Mononuclear Cells and Granulocytes from Human Blood;" pp. 77-89.
S. Haynesworth, M. Baber, an I. Caplan; "Cell Surface Antigens on Human Marrow-Derived Mesenchymal Cells are Detected by Monoclonal Antibodies;" 1992; pp. 69-80.
S. Luh, C. Tsai, W. Shau, J. Chen, S. Kuo, S. Lin-Shiau, Y. Lee; "The Effects of Inhaled Nitric Oxide, Gabexate Mesilate, and Retrograde Flush in the Lung Graft from Non-Heart Beating Minipig Donors;" May 2000; pp. 2019-2027.
S. Kubalak; W. Miller-Hance; T. O'Brien; E. Dyson; and K. Chien; "Chamber Specification of Atrial Myosin Light Chain-2 Expression Precedes Septation during Murine Cardiogenesis;" Nov. 1993; pp. 16961-16970.
J. Ringe, C. Kaps, B. Schmitt, K. Buscher, J. Bartel, H. Smolian, O. Schultz, G. Burmester, T. Haupl, M. Sittinger; "Porcine Mesenchymal Stem Cells: Introduction of Distinct Mesenchymal Cell Lineages;" Mar. 2001; pp. 321-327.
I. Skerjanc, H. Petropoulos, A. Ridgeway, and S. Wilton; "Myocyte Enhancer Factor 2C and Kkx2-5 Up-regulate each other's Expression and Initiate Cardiomyogenesis in P19 Cells." May 1998; pp. 34904-34910.
W. Wright, D. Sassoon, V. Lin; "Myogenin, a Factor Regulating Myogenesis, has a Domain Homologous to MyoD;" Feb. 1989; pp. 607-617.
Z. Chen, G. Friedrich, and P. Soriano; "Transcriptional Enhancer Factor 1 Disruption by a Retroviral Gene Trap Leads to Heart Defects and Embryonic Lethality in Mice;" Jul. 1994; pp. 2293-2301.
S. Makino, K. Fukuda, S. Miyoshi, F> Konishi, H. Kodoma, J. Pan, M. Sano, T. Takahashi, S. Hori, H. Abe, J. Hata, A. Umezawa, S. Ogawa; "Cardiomyocytes can be Generated from Marrow Stromal Cells In Vitro;" Mar. 1999; pp. 697-705.

* cited by examiner

*Primary Examiner*—Joanne Hama
(74) *Attorney, Agent, or Firm*—Thomas, Kayden, Horstemeyer & Risley

(57) ABSTRACT

Methods are provided for producing cardiomyocytes suitable for various medical applications. In one embodiment, a method of producing cardiomyocytes is provided, which comprises culturing mesenchymal stem cells in a medium containing ascorbic acid. In another embodiment, such method further comprises the step of selecting fast-growing mesenchymal stem cell clones before culturing the selected clones in the culturing medium that contains ascorbic acid.

3 Claims, 6 Drawing Sheets
(3 of 6 Drawing Sheet(s) Filed in Color)

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Chemically Synthesized Forward Primer Sequence

<400> SEQUENCE: 1
gtggatcacc aagcaggagt                                                    20

<210> SEQ ID NO 2
<211> LENGTH: 19
<212> TYPE: DNA
<213> ORGANISM: Artificial Sequence
<220> FEATURE:
<223> OTHER INFORMATION: Chemically Synthesized Reverse Primer Sequence

<400> SEQUENCE: 2
gcagcataac agaatggct                                                     19

<210> SEQ ID NO 3
<211> LENGTH: 21
<212> TYPE: DNA
<213> ORGANISM: Artificial Sequence
<220> FEATURE:
<223> OTHER INFORMATION: Chemically Synthesized Forward Primer Sequence

<400> SEQUENCE: 3
tcgggacctc actgactacc t                                                  21

<210> SEQ ID NO 4
<211> LENGTH: 21
<212> TYPE: DNA
<213> ORGANISM: Artificial Sequence
<220> FEATURE:
<223> OTHER INFORMATION: Chemically Synthesized Reverse Primer Sequence

<400> SEQUENCE: 4
gccagcagat tccataccaa t                                                  21

<210> SEQ ID NO 5
<211> LENGTH: 20
<212> TYPE: DNA
<213> ORGANISM: Artificial Sequence
<220> FEATURE:
<223> OTHER INFORMATION: Chemically Synthesized Forward Primer Sequence

<400> SEQUENCE: 5
gggcatgaac catgagaagt                                                    20

<210> SEQ ID NO 6
<211> LENGTH: 20
<212> TYPE: DNA
<213> ORGANISM: Artificial Sequence
<220> FEATURE:
<223> OTHER INFORMATION: Chemically Synthesized Reverse Primer Sequence

<400> SEQUENCE: 6
aagcagggat gatgttctgg                                                    20

<210> SEQ ID NO 7
<211> LENGTH: 21

<212> TYPE: DNA
<213> ORGANISM: Artificial Sequence
<220> FEATURE:
<223> OTHER INFORMATION: Chemically Synthesized Forward Primer Sequence

<400> SEQUENCE: 7
ttgacagctt gagcagctgt a                                    21

<210> SEQ ID NO 8
<211> LENGTH: 20
<212> TYPE: DNA
<213> ORGANISM: Artificial Sequence
<220> FEATURE:
<223> OTHER INFORMATION: Chemically Synthesized Reverse Primer Sequence

<400> SEQUENCE: 8
catgttgccc atccttcaga                                      20

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized Forward Primer Sequence

<400> SEQUENCE: 9
cctgctggag gacaagtacc                                      20

<210> SEQ ID NO 10
<211> LENGTH: 20
<212> TYPE: DNA
<213> ORGANISM: Artificial Sequence
<220> FEATURE:
<223> OTHER INFORMATION: Chemically Synthesized Reverse Primer Sequence

<400> SEQUENCE: 10
gtgagctctg attggacacg                                      20

<210> SEQ ID NO 11
<211> LENGTH: 20
<212> TYPE: DNA
<213> ORGANISM: Artificial Sequence
<220> FEATURE:
<223> OTHER INFORMATION: Chemically Synthesized Forward Primer Sequence

<400> SEQUENCE: 11
ccacttctat gacggggaaa                                      20

<210> SEQ ID NO 12
<211> LENGTH: 20
<212> TYPE: DNA
<213> ORGANISM: Artificial Sequence
<220> FEATURE:
<223> OTHER INFORMATION: Chemically Synthesized Reverse Primer Sequence

<400> SEQUENCE: 12
ggtccacaga cacggacttc                                      20

<210> SEQ ID NO 13
<211> LENGTH: 20
<212> TYPE: DNA
<213> ORGANISM: Artificial Sequence
<220> FEATURE:
<223> OTHER INFORMATION: Chemically Synthesized Forward Primer Sequence

<400> SEQUENCE: 13

```
aagagctgtg cgcgctgcag                                              20

<210> SEQ ID NO 14
<211> LENGTH: 20
<212> TYPE: DNA
<213> ORGANISM: Artificial Sequence
<220> FEATURE:
<223> OTHER INFORMATION: Chemically Synthesized Reverse Primer Sequence

<400> SEQUENCE: 14
agagtctggt cctgcgcgtg                                              20

<210> SEQ ID NO 15
<211> LENGTH: 21
<212> TYPE: DNA
<213> ORGANISM: Artificial Sequence
<220> FEATURE:
<223> OTHER INFORMATION: Chemically Synthesized Forward Primer Sequence

<400> SEQUENCE: 15
tcaacttcat ccacaagctc a                                            21

<210> SEQ ID NO 16
<211> LENGTH: 21
<212> TYPE: DNA
<213> ORGANISM: Artificial Sequence
<220> FEATURE:
<223> OTHER INFORMATION: Chemically Synthesized Reverse Primer Sequence

<400> SEQUENCE: 16
tatccctgtt tgttaccacc a                                            21
```

METHOD OF PRODUCING CARDIOMYOCYTES FROM MESENCHYMAL STEM CELLS

FIELD OF THE INVENTION

The present invention relates to cardiomyocytes that are suitable for cell therapy and the preparation method thereof. More particularly, the present invention provides a method of producing cardiomyocytes by culturing bone marrow mesenchymal stem cells in a culture medium containing ascorbic acid.

BACKGROUND OF THE INVENTION

Mesenchymal stem cells (MSCs) are multipotent, and are capable of differentiating into more than one type of mesenchymal cell lineage, such as adipocytes, cardiac muscle cells and skeletal muscle cells (Galmiche et al., (1993) Blood 82:66-76; and Wakitani et al., (1995) Muscle Nerve 18:1417-1426). Thus, MSCs has gained considerable interest as a treatment for a myriad of diseases, conditions, and disabilities because they provide a renewable source of cells and tissues, and most importantly, unlike embryonic stem cells, mesenchymal stem cells pose no ethical dilemma in using them as a cell source.

Bone marrow mesenchymal stem cells (BMSCs) have been show shown to differentiate into cardiomyocyte-like cells by use of a DNA demethylating agent (e.g., 5-azacytidine) or by co-culturing with rodent cardiomyocytes. However, 5-azacytidine is cytotoxic and co-culturing with rodent cells runs the risk of causing xeno-contamination to the recipient of the cells. In this regard, improved methods have been proposed.

WO 2004/065589 A1 disclosed a method of producing cells for transplantation into myocardial tissue. According to Example 1 of '589 patent, BMSCs were first isolated and cultured in a medium containing 10% fetal bovine serum, 100 μM L-ascorbic acid-2-PO$_4$, 5-15 ng/ml human LIF (leukemia inhibitory factor) and 20 nM dexamethasone. This medium allows the BMSCs to maintain their self-renewing character and to expand by passaging without losing responsiveness to the differentiation agents such as growth factors. Induction of BMSCs into cardiomyocytes were achieved by culturing BMSCs in the presence of growth factors (50 ng/ml bFGF and 25 ng/ml BMP-2) and IGF-1 (2 ng/ml) for 2 weeks.

WO 2005/056779 disclosed a method of producing cells for transplantation into myocardial tissue of a mammal comprising culturing bone marrow stem cells in a cardiac specific media contain bFGF, BMP-2 and IGF-1, and preferably, the media contain bFGF, BMP-2 and IGF-1 in each concentration of 1 to 200 ng/ml, and further contain 2 to 20% fetal bovine serum, 1 to 1000 μL-ascorbic acid-2-phosphate, 5 to 15 ng/ml leukemia inhibitory factor (LIF) and 1 to 200 nM dexamethasone.

U.S. Pat. No. 6,387,369 disclosed a method of producing cardiomycetes in vivo by administering to the heart of an individual, such as a human, a cardiomyocyte producing amount of mesenchymal stem cells. The MSCs were administered as a liquid injectable to the heart or as a preparation of cells in a matrix which is or becomes solid or semi-solid. The specification also teaches treatment of MSCs including the steps of treating MSCs with growth factors and differentiating agents as well as exposure of MSCs to mechanical stimuli and electrical stimulation, so that the treated MSCs may progress towards cardiomyocytes. However, it did not point out the exact species of suitable growth factors and/or differentiating agents.

Shim et al (Shim et al., (2004) BBRC 324:481-488) disclosed the use of cardiomyogenic differentiation medium containing insulin, dexamethasone and ascorbic acid. Differentiation was confirmed by the expression of cardiomyocyte-specific proteins such as cardio troponin I, sarcomeric tropomyosin and cardiac titin.

All of the above-identified publications teach differentiation of MSCs by use of a cardiomyogenic differentiation medium, which is a combination of several agents including hormones (e.g., insulin); growth factors (e.g., bFGF and IGF); serum and other agents such as immuno-suppressing agent (e.g., dexamethasone and LIF) and vitamin (e.g., ascorbic acid). There is also a publication that teaches the use of a more simplified cardiomyogenic differentiation medium, however, this differentiation medium was used to differentiate embryonic stem cells (ESCs), instead of bone marrow mesenchymal stem cells. For example, Takahashi et al (Takahashi et al., (2003) Circulation, 107:1912-1916) disclosed the induction of differentiation of ESCs into cardiomyocytes by 0.01 mM ascorbic acid (see FIG. 2 of Takahashi et al), and this effect of ascorbic acid is not mimicked by the other antioxidants such as N-acetylcysteine, Tiron or vitamin E (see FIG. 5 of Takahashi et al). However, the role of ascorbic acid in induction of cardiac differentiation of ESCs is still controversial. Another publication, WO 2005/065354, disclosed the use of a defined medium in maintaining the undifferentiated growth of human ESCs, said medium comprises sufficient amounts of bFGF, insulin, and ascorbic acid (see claim 1 of '354 patent). Example 8 of '354 patent, which is directed to a method of inducing cardia differentiation, was accomplished by culturing the undifferentiated human ESCs in a standard differentiation media consisting of KO-DMEM (80%), defined FBS (20%), L-glutamine (2 mM), MEM nonessential amino acids (1×) and β-mercaptoethanol (100 μM); and beating cardiomyocytes were observed in about 1 week, increased in numbers with time, and retained contractility for over two months. In other words, Example 8 of '354 patent implicates that the induction of human ESCs into cardiomyocytes may be achieved in the absence of ascorbic acid.

In view of the above, to date, there isn't any publication discloses the use of ascorbic acid in induction of differentiation of bone marrow mesenchymal stem cells into cardiomyocytes, and there exists in this art a need of an improved method of producing cardiomyocytes from bone marrow mesenchymal stem cells, such method is simple to use and with high producing rate that large amount of differentiated cardiomyocytes may be obtained in a relatively short period of time to ensure a successful cell-based therapy.

SUMMARY

The object of this invention is to provide cardiomyocytes that are suitable for cell therapy such as tissue transplant. Thus, in one aspect, the invention provides a method of producing cardiomyocytes, which is simple, safe and with producing rate of cardiomyocytes between 20% to 35%, preferably, 25%. In another aspect, this invention provides cardiomyocytes that have been derived using the above method to treat heart diseases such as myocardial infarction.

In one preferred embodiment, the invention provides a method of producing cardiomyocytes by culturing the mesenchymal stem cells (MSCs) in a medium containing ascorbic acid. In the method of this invention, the mesenchymal stem cells are isolated from bone marrow and 20% to 35%, preferably, 25% of the MSCs will differentiate into cardiomyocytes upon induction by ascorbic acid. Preferably, the medium is I'MEM and supplemented with 10% fetal bovine serum (FBS), and further contains ascorbic acid in an amount between 100 μM to 10 mM, and preferably, 1 mM.

In another preferred embodiment, the invention provides a method of producing cardiomyocytes, further comprises the step of selecting single fast-growing MSCs clones before culturing the selected MSCs clones in a medium containing ascorbic acid. According to this method, the fast-growing MSCs clones have a doubling time of less than 25 hrs. With the combination of selecting fast-growing MSCs and culturing the selected MSCs clones in a medium containing ascorbic acid, and 20% to 35%, preferably, 25% of the cultured cells are cardiomyocytes.

In still another preferred embodiment, this invention provides cardiomyocytes prepared in accordance with the method of this invention, said cardiomyocytes express specific cardiac markers and/or proteins, and are suitable for transplantation and treating heart diseases. The cardiomyocytes prepared in accordance with the method of this invention are more suitable than those prepared by using demethylating agent such as 5-azacytidine.

These and other aspects and advantages will become apparent when the Description is read in conjunction with the accompanying Examples. It is to be understood that both the foregoing general description and the following detailed description are by examples, and are intended to provide further explanation of the invention as claimed.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The accompanying drawings are included to provide a further understanding of the invention, and are incorporated in and constitute a part of this specification. The drawings illustrate embodiments of the invention and, together with the description, serve to explain the principles of the invention. In the drawings, FIG. 1 are photographs showing the morphology of porcine mixed MSCs treated with 5-azacytidine (A), ascorbic acid (B), DMSO(C), retinoic acid (D), ethyl alcohol (E) and medium (F) in accordance with one preferred embodiment of this invention.

DESCRIPTION OF THE INVENTION

Figure 1:
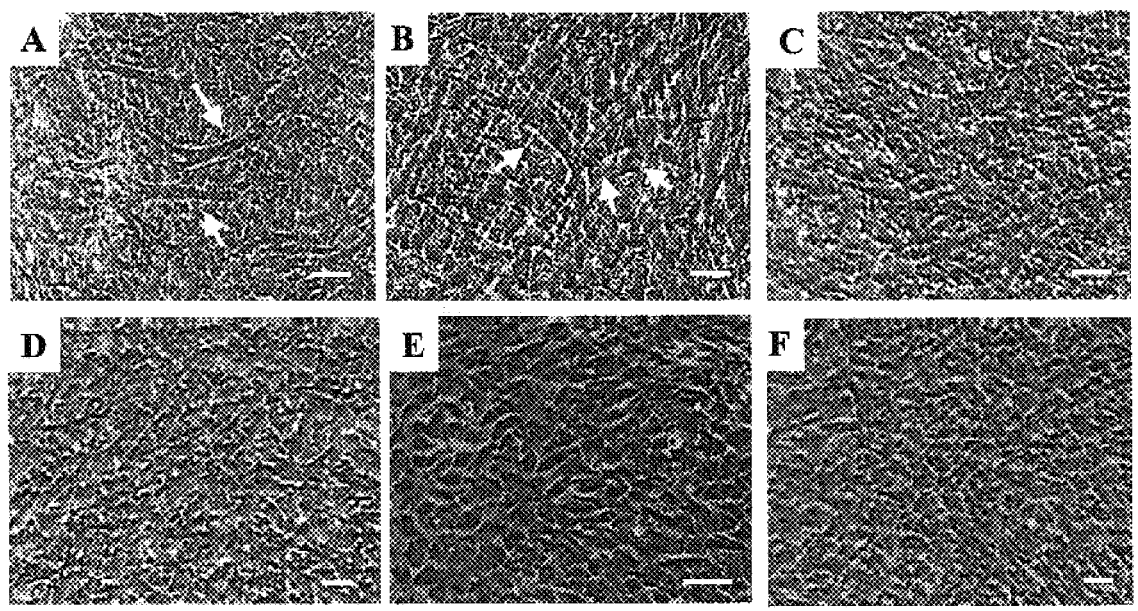

The embodiments described and the terminology used herein are for the purpose of describing exemplary embodiments only, and are not intended to be limiting. The scope of the present invention is intended to encompass additional embodiments not specifically described herein, but that would be apparent to one skilled in the art upon reading the present disclosure and practicing the invention.

The present invention is directed to an improved method for generating cardiomyocytes suitable for use in various clinical applications, such as tissue transplantation and treating heart diseases.

Thus in one embodiment, the invention provides a method of producing cardiomyocytes by culturing mesenchymal stem cells in a medium containing ascorbic acid.

Mesenchymal stem cells are obtained by collecting a single-cell suspension of mononuclear cells from bone marrow and/or umbilical cord blood The bone marrow aspirates may obtain from a suitable donor or any commercial source. The post-partum umbilical cord may obtain, for example, with informed consent from a woman underwent caesarian procedure or normal birth. The cord blood may be drawn and collected by a syringe. A single-cell suspension of mononuclear cells may be prepared by centrifugation according to a procedure described by Boyum A., Scand. J. Clin. Lab. Invest. 21 Suppl. 97 (Paper IV): 77-89, 1968. The obtained mononuclear cells are then seeded onto culture dishes in a culture medium at 37° C. in an atmosphere of 5% $CO_2$. The culture medium comprises standard medium, such as α-MEM (Gibco) containing 100 unit/ml penicillin, 100 μg/ml streptomycin (Gibco) and 20% fetal bovine serum (FBS), and may be optionally supplemented with growth factors such as fibroblast growth factors (FGFs) as appropriate.

To induce cardiac differentiation, the mesenchymal stem cells isolated and cultured in accordance with the above-described method were changed to I'MEM (Gibco) medium supplemented with 10% FBS for a day and then treated with ascorbic acid, preferably in an amount of about 100 μM to about 10 mM, most preferably, 1 mM, for at least 4 weeks. After 4 weeks in culture, the differentiated MSCs would connect to adjoining cells via intercalated disc and started to form myotubes in the cytoplasm. The characteristic multi-nucleated structure and myotube structure of myocytes can be visualized under phase contrast microscope and/or fluorescence microscope after immunohistochemical staining. In one preferred embodiment, the characteristic myotube structure and multi-nucleated structure of a muscle cell are detected by staining with fluorescent dye such as phallacidine and propidium iodide, to reveal the formed myofibrils and the multinucleated structure.

The differentiated MSCs may also be identified by the expression of cardiac specific markers within the myocytes. These markers include, but are not limited to, GATA4, Nkx 2.5, ACTA, ACTC, myogenin, Tef-1, and myosin enhancing factor such as Mef-2c and Mef-2d. In one preferred embodiment, the expression of ACTA, Mef-2d and myogenin were enhanced by ascorbic acid treatment. Differentiated cardiomyocytes can also be identified by the expression of cardiac differentiation markers, such as myosin heavy chain (MHC), myosin light chain (MLC), cardiac troponin I, cardiac troponin T, α-cardiac actin, α-actinin, and connexin43. In one preferred embodiment, the expression of cardiac troponin I was enhanced by ascorbic acid treatment. The identification of cardiac-related cell markers can be detected by, for example, reporter gene expression, RNA expression (RT-PCR and Northern Blot) or protein expression (immunofluorescene assay, Western Blot and flow cytometry). All these assays are well known in the relevant art and can be practiced by any skilled person in this art without undue experiment.

In one preferred embodiment, the isolated mononuclear cells, i.e., mesenchymal stem cells, may undergo a further selecting step before being differentiated into cardiomyocytes. Particularly, fast-growing MSCs clones with a doubling time of less than 25 hrs were selected. The inventors identified that MSCs actually were comprised of two distinct populations of cells, i.e., fast-growing MSCs and slow-growing MSCs. The identified fast-growing MSCs are characterized in having a doubling time of less than 25 hours, whereas the slow-growing MSCs are characterized in having a doubling time of greater than 100 hours. With the combination of the steps of selecting fast-growing MSCs and culturing the selected MSCs clones in a medium containing ascorbic acid, cardiac differentiation was significantly enhanced, and 20% to 35%, preferably, 25% of the cells are identified to be cardiomyocytes.

The cardiomyocytes prepared in accordance with the method of this invention are more suitable than those prepared by using demethylating agent such as 5-azacytidine, which is known to cause hypomethylation of DNA and exert a cytotoxic effect on rapid dividing cells. Thus, the cardiomyocytes prepared in accordance with the method of this invention may be used as a cell source in cell-based therapy for repairing damage heart tissues and/or tissue transplant. The cardiomyocytes may be administered through several routes, including, but are not limited to, direct intracardiac muscle injection, in which cardiomyocytes may be in an injectable liquid suspension preparation or in a biocompatible medium that is injectable in liquid form and becomes semi-solid at the site of damaged myocardium; intravenous injection; or open surgery that involves direct physical access to the heart.

The singular forms "a", "and", and "the" are used herein to include plural referents unless the context clearly dictates otherwise.

All other acronyms and abbreviations have the corresponding meaning as published in journals related to the arts of chemistry and biology.

Other than in the operating examples, or where otherwise indicated, all numbers expressing quantities of ingredients, reaction conditions, and so forth used in this application are to be understood as being modified in all instances by the term "about." Accordingly, unless the contrary is indicated, the numerical parameters set forth in this application are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements.

All publications mentioned in this application are incorporated by reference to disclose and describe the methods and/or materials in connection with which the publications are cited. Additionally, the publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Methods, techniques, and/or protocols (collectively "methods") that can be used in the practice of the invention are not limited to the particular examples of these procedures cited throughout the specification but embrace any procedure known in the art for the same purpose. Furthermore, although some methods may be described in a particular context in the specification, their use in the instant invention is not limited to that context.

EXAMPLES

The following Examples are provided to illustrate certain aspects of the present invention and to aid those of skilled in the art in practicing this invention. These Examples are in no way to be considered to limit the scope of the invention in any manner.

Example 1

Isolation and Culture of Bone Marrow Stem Cells (BMSCS)

1.1 Isolation and Culture of Porcine BMSCs

Porcine bone marrow mononucleated cells were purified according to a protocol described by Haynesworth et al (Haynesworth et al., (1992) Bone 13(1), 81-8). Briefly, bone marrows from posterior iliac crest bones of three 6-8 months old Lee-Sung miniature pigs (Luh et al., (2000) Transplantation 69(10), 2019-2027) (3045 kg) were aspirated into syringes that contained 6,000 unit heparin. The marrow samples were diluted in a ratio of 1:1 with HBSS (Gibco) and loaded onto 1.073 g/mL Ficoll solution (Amersham) in 50 mL centrifugations tubes and were centrifuged at 2,000 rpm for 40 min at room temperature. The mononucleated cells were collected from upper and interface layers, and washed with HBSS (Gibco) twice. Subsequently, the cells were cultured in αMEM (Hyclone) medium containing 100 unit/ml penicillin, 100 μg/ml streptomycin (Gibco) and 20% fetal bovine serum (FBS) from a selected lot (Gibco, Lot No.: 1149239) at 37° C. in humid air with 5% $CO_2$. After a series of continuously cultures, the non-adhesive cells were removed by medium change. Porcine mixed mesenchymal stem cells (MSCs) thus obtained may be used directly in the differentiation experiment of example 1.3 and can be successfully propagated for at least 2 months.

1.2 Isolating Fast-Growing Single BMSCs Clones

The porcine mixed MSCs of example 1.1 were collected from upper and interface layers, and then seeded at limited dilution into culture. Briefly, $1 \times 10^4$ mononucleated cells were plated in each well of a 96-multiwell plate, washed with HBSS (Gibco) twice, and then cultured in αMEM (Hyclone) containing 20% FBS from selected lots at 37° C. in humid air with 5% $CO_2$. Non-adhesive cells were removed by medium change and the number of the remaining cells attached to the bottom of culture wells was examined under the microscope. Clones from wells containing only a single cell attached were chosen for further study. The isolated cells were further cultured for 3 passages, and then frozen in liquid nitrogen until the differentiation studies.

Figure 2:
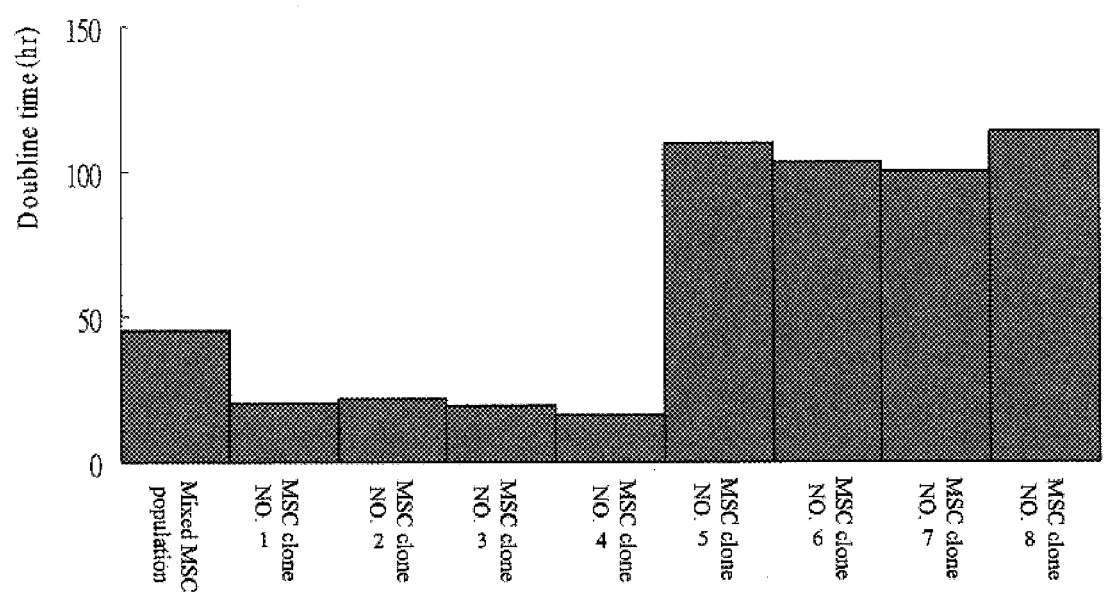
FIG. 2 illustrates the doubling time of mixed MSCs population and selected MSCs clones No.: 1 to 8 in accordance with one preferred embodiment of this invention.

For selecting the fast-growing single BMSCs clones, the nucleated cells were seeded onto 1,000 wells following limited dilution in culture ($10^4$ cells/well), and 120 clones, each of which was derived from a single attached cell in the well, were obtained. Morphologically, all of the clones comprised a relatively homogeneous population of fibroblast-like cells at subconfluence, while at confluence the cells appeared more polygonal and formed a tight packed monolayer. Two populations according to growth rate in primary culture were identified: one is the highly proliferative MSC clones (such as clone Nos. 1-4 in FIG. 2), which had a doubling time of less than 25 hours (20.2, 21.7, 19.2 and 16.2 hours, respectively); another is the slow proliferative MSC clone (such as clone Nos. 5-8 in FIG. 2) with a doubling time of greater than 100 hours. In general, both fast-growing and slow-growing cells showed morphologies similar to fibroblastic elongated cells, namely, large flattened cells and thin shaped cells as described previously (Ringe et al., (2002) Cell Tissue Research(307), 321-327).

Example 2

Induction of Cardiomyocytes from BMSCs 2.1 Cardio Differentiation by Ascorbic Acid Treatment BMSCs of example 1.1 ($10^4$ cells/cm$^2$) were cultured in αMEM (Hyclone) containing 20% FBS for 2 days and then the medium was changed to I'MDM (Gibco) containing 10% FBS for another day, then various differentiation agents such as 5-azacytidine (3 µM), ascorbic acid (1 mM), DMSO (0.5%) or retinoic acid ($10^{-9}$M) was added to induce myotubes formation. After 4 weeks of culture in the presence of the above-identified differentiation agents, morphologic appearance of differentiated MSCs were confirmed by the formation of myotubes for cells that were cultured in the presence of 5-azacytidine (FIG. 1A) and ascorbic acid (FIG. 1B), with differentiation rate of about 10% (5~15%) and 25% (20~35%), respectively; whereas the neuronal differentiating agent—retinoic acid (FIG. 1D), ethyl alcohol (solvent for dissolving retinoic acid, in 1:1000 dilution, FIG. 1E) and medium (FIG. 1F) had no effect on cardio differentiation.

Figure 3:
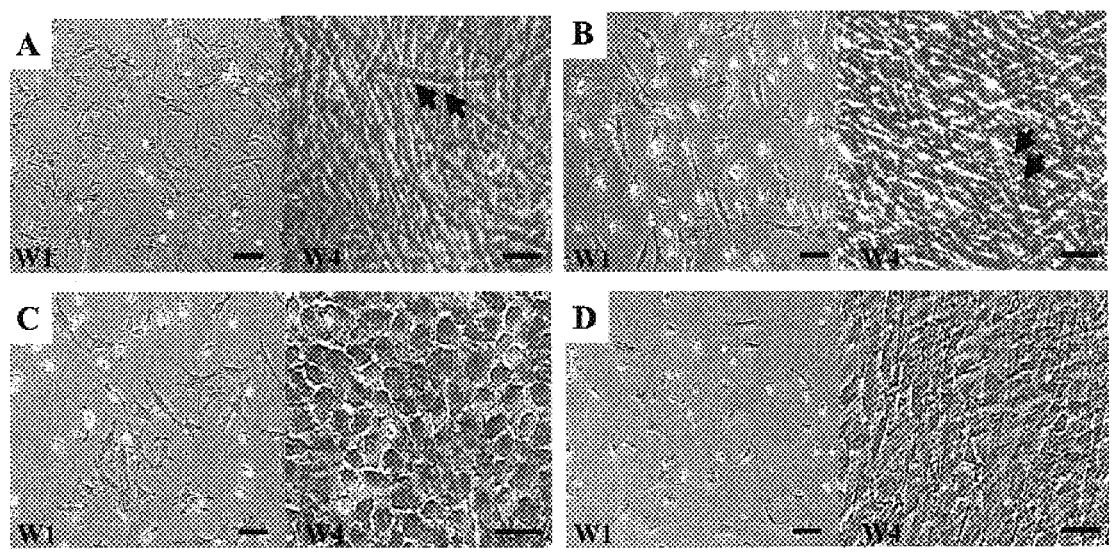
FIG. 3 are photographs showing the morphology of mixed MSCs and selected MSCs clones before (W1, left panel) and after (W4, right panel) ascorbic acid treatment, in which (A) is mixed MSCs with a doubling time of 45 hrs, (B) is the fast-growing clone No. 1 with a doubling time of less than 25 hrs; (C) is the slow-growing clone No. 8 with a doubling time of greater than 100 hrs, and (D) is the control MSCs without ascorbic acid treatment, scar bar=80 μm.

To examine the cardiogenic potential of single BMSCs clones, mixed MSCs of example 1.1 and isolated single BMSCs clones of example 1.2 (both fast-growing clones of clones 1-4 and slow-growing clones of clones 5-8) were cultured in the presence of 1 mM ascorbic acid for 4 weeks, and one representative result was illustrated in FIG. 3. Before ascorbic acid treatment, there were no differences in terms of morphology among mixed population of MSCs (FIG. 3A), fast-growing clone No. 1 (FIG. 3B) and slow-growing clone No. 8 (FIG. 3C), respectively. In contrast, after ascorbic acid treatment, mixed MSCs (FIG. 3A) and fast-growing clone No. 1 (FIG. 3B) started to form myotube-like structures from the third week; and both MSC control (without ascorbic acid treatment, FIG. 3D) and slow-growing clone No. 8, (with ascorbic acid treatment, FIG. 3C) retained a fibroblast-like morphology after 4 weeks. This result indicated that the fast-growing clones of BMSCs are the populations of BMSCs that possess the ability of being differentiated into cardiomyocytes upon induction by ascorbic acid.

2.2 Myotube Formation Detected by Immunohistochemistry

Figure 4:
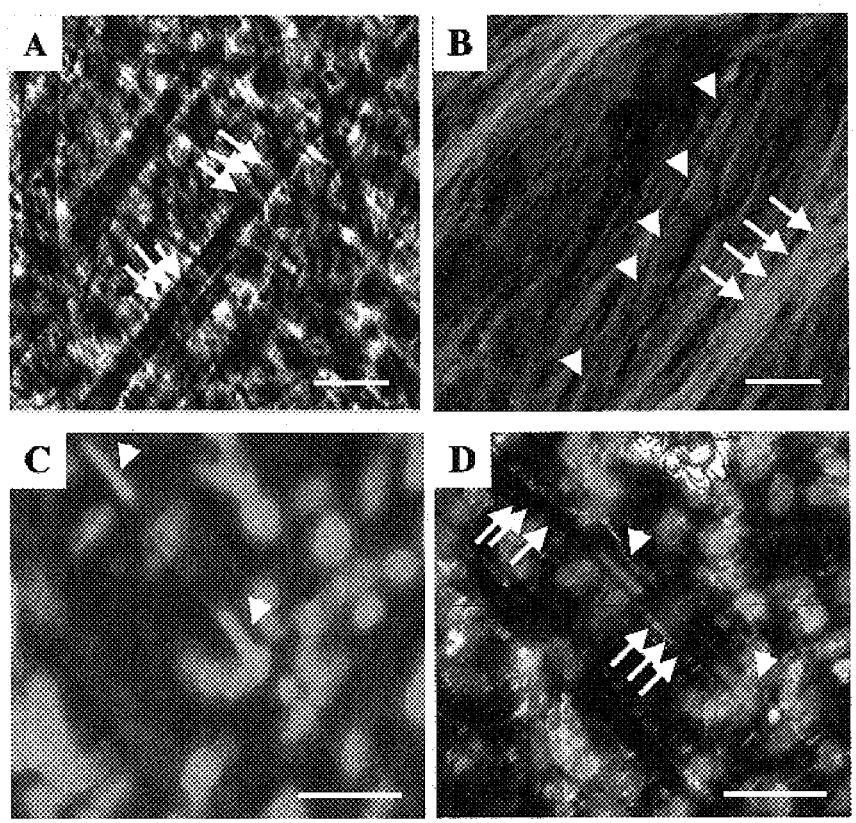
FIG. 4 are photographs showing the myotubes morphology of differentiated MSCs induced by ascorbic acid, in which (A) is the phase contrast photograph showing myotubes formed in the cytoplasm indicated by arrows, (B) is the confocal microscropy photograph showing multinuclears stained with DAPI appear in red color and indicated by arrowheads and myotubes stained with phallacidin appear in green color and indicated by the arrowheads, (C) is the fluorescent microscopy photograph stained with Hoechost 33342 showing a myotube with two-nucleates structure, (D) is the photograph showing myotubes with multi-nuclear structure confirmed by immunostaining, scar bar=80 μm.

To further verify the myotube formation by ascorbic acid induction, the differentiated MSCs were stained with fluorescent phallacidin, which binds to F-actin, to reveal the formed myofibrils under phase contrast microscope (FIG. 4A) and fluorescence microscope (FIGS. 4B, 4C, and 4D), respectively. Briefly, the differentiated MSCs were washed three times with PBS for 3 minutes and the cells were then fixed with 4% paraformaldehyde for 15 min, and normalized with 0.1M glycine for 5 min, and permeabilized with 0.1% Tween 20 for 1 min. The myotube formation was confirmed by treating with alexa flour 488-conjugate phallacidin (Molecular Probes) for 20 min at room temperature. The cells were then washed two or more times with PBS. The multi-nucleate myotubes were stained by propidium iodide (Sigma) for 5 min at room temperature. After washing, they were mounted and observed under confocal laser scanning microscopy, and the multinucleated myotubes, which are one of the characteristics of fused myogenic cells, were detectable by propidium iodide staining (FIGS. 4B, 4C, and 4D).

2.3 Expression of Myogenic Associated Genes and Proteins Following Induction of Myogenic Differentiation The effect of ascorbic acid on the expression of myogenic associated genes and proteins were examined by Reverse-transcription polymerase chain reaction (RT-PCR) (FIG. 5) and western blot (FIG. 6), respectively.

RT-PCR Total RNA was extracted from differentiated MSCs using a RNA mini Kit (e.g., QIAGEN). Subsequently, cDNA was synthesized from 1 µg of extracted total RNA using a ThermoScript RT-PCR kit (Invitrogen). The PCR reaction was carried out with Taq DNA polymerase (Invitrogen). Reverse-transcription polymerase chain reaction (RT-PCR) of myogenic associated genes, including actin, alpha 1, skeletal muscle (ACTA), actin, alpha, cardiac muscle (ACTC) (Kubalak et al., (1994) J. Biol. Chem. 269(24), 16961-16970), mef-2c, mef-2d (Skerjanc et al., (1998) J. Biol. Chem. 273(52), 34904-34910), myogenin (Wright et al., (1989) Cell 56(4), 607-617), nkx2.5 (Lints et al., (1993) Transplantation 69(10), 2019-2027) and tef-1 (Chen et al., (1994) Genes Dev 8(19), 2293-2301), were performed on the differentiated cell samples (Table 1). The relative expression level of glyceraldehyde 3-phosphate dehydrogenase (GAPDH) was used as an internal control for each sample, and porcine heart and skeletal muscle cells were used as a positive control of differentiation pathway. A spectrophotometer (Amersham Bioscience) and Agilent 2100 Bioanalyzer (Agilent Technologies) were used to measure the total RNA of concentration and integrity, respectively. Results were illustrated in FIG. 5.

TABLE 1

The PCR Primer Sequence

| Gene | Gene Bank Assess No. | Primer Sequence/Product Size (bp) | SEQ ID NO: |
|---|---|---|---|
| ACTA | U16368 | 5'-GTGGATCACCAAGCAGGAGT-3' | 1 |
|  |  | 5'-GCAGCATAACAGAATGGCT-3' | 2 |
|  |  | 309 |  |

TABLE 1-continued

The PCR Primer Sequence

| Gene | Gene Bank Assess No. | Primer Sequence/Product Size (bp) | SEQ ID NO: |
|---|---|---|---|
| ACTC | NM_009608/NM_005159 | 5'-TCGGGACCTCACTGACTACCT-3' | 3 |
| | | 5'-GCCAGCAGATTCCATACCAAT-3' | 4 |
| | | 274 | |
| GAPDH | AF017079 | 5'-GGGCATGAACCATGAGAAGT-3' | 5 |
| | | 5'-AAGCAGGGATGATGTTCTGG-3' | 6 |
| | | 230 | |
| Mef-2c | NM_025282/NM_002397 | 5'-TTGACAGCTTGAGCAGCTGTA-3' | 7 |
| | | 5'-CATGTTGCCCATCCTTCAGA-3' | 8 |
| | | 159 | |
| Mef-2d | AJ519843 | 5'-CCTGCTGGAGGACAAGTACC-3' | 9 |
| | | 5'-GTGAGCTCTGATTGGACACG-3' | 10 |
| | | 137 | |
| Myogenic | U14331 | 5'-CCACTTCTATGACGGGGAAA-3' | 11 |
| | | 5'-GGTCCACAGACACGGACTTC-3' | 12 |
| | | 203 | |
| Nkx 2.5 | NM_008700/NM_4378 | 5'-AAGAGCTGTGCGCGCTGCAG-3' | 13 |
| | | 5'-AGAGTCTGGTCCTGCGCGTG-3' | 14 |
| | | 273 | |
| Tef-1 | L13853/NM_63896 | 5'-TCAACTTCATCCACAAGCTCA-3 | 15 |
| | | 5'-TATCCCTGTTTGTTACCACCA-3' | 16 |
| | | 99 | |

Western Blot Total protein from the differentiated MSCs were extracted with cell lysis buffer (Pierce) containing 1× protease inhibitor cocktail (Roche). Protein concentration was determined by a Bio-Rad protein assay kit. Samples were boiled for 5 minutes and then subjected to 12.5% polyacrylamide gel electrophoresis. Proteins in gel were electrophoretically transferred to polyvinylidene diflouride membrane (PVDF, Millipore) at 4° C. for overnight in 25 mM Tris, 190 mM glycine (pH 8.3) containing 0.01% SDS and 10% methanol. The membrane was blocked with 5% non-fat milk to prevent nonspecific binding and then incubated with one of three primary antibodies. Subsequently, the membrane was stained with primary antibodies that were against cardiac troponin I (at a dilution of 1:1000) and connexin43 (at a dilution of 1:2000) (Chemicon) (Makino et al., (1999) J. Clin. Invest. 103(5), 697-705), respectively, for 1 hour at room temperature. As a control, membrane was also probed with anti-actin antibody (at a dilution of 1:1000) (Lab Vision). Unbound antibodies were removed by four washings of PBS-0.1% Tween 20 buffer (pH 7.4), each washing lasted for 5 minutes. Bound antibodies were recognized by horseradish peroxidase-conjugated goat anti-mouse IgG and ECL reagent (Pierce), and detected by chemiluminescent detection.

Figure 5:
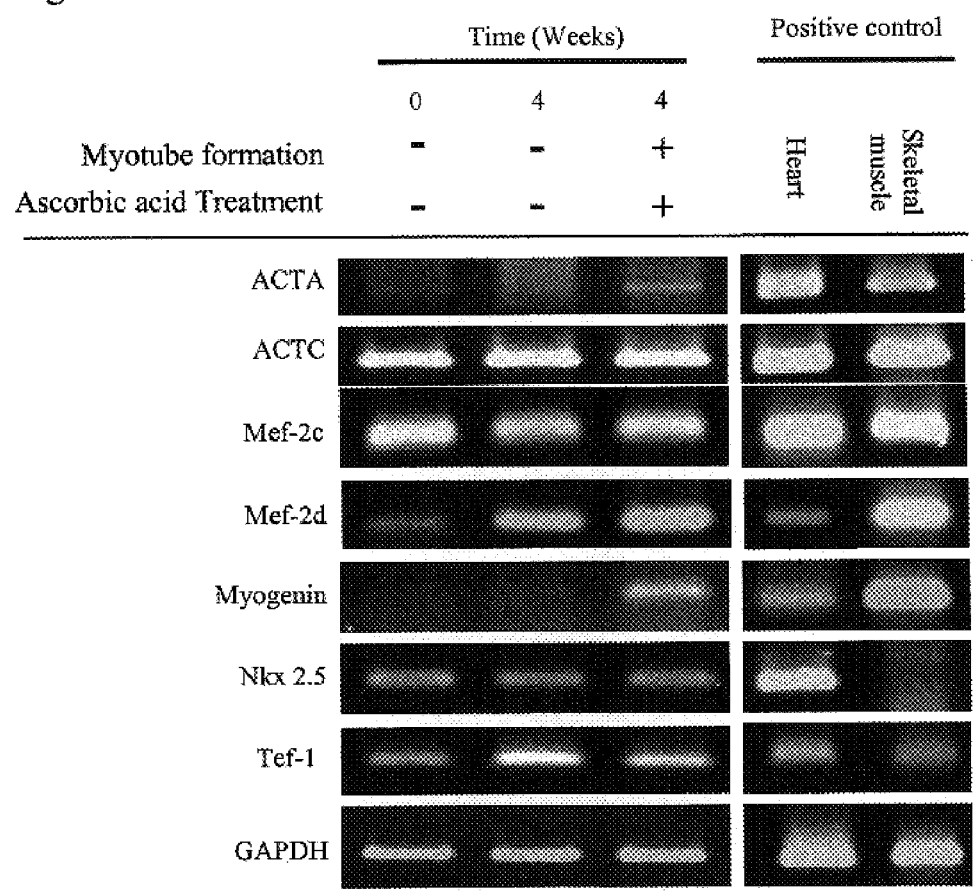
FIG. 5 illustrates the expression pattern of various cell markers analyzed by RT-PCR in MSCs treated with or without ascorbic acid.

It is clear from FIG. 5 that the expression of the ACTA, mef-2d and myogenin genes increased significantly after ascorbic acid treatment. The tef-1 gene expression was induced spontaneously during the cell culture period. Some myogenic associated genes, such as ACTC, nkx2.5 and mef-2c, showed no significant change over the course of differentiation. The expression patterns are similar to the results of cardiomyocytes induction from marrow stromal cells treated with 5-azacytidine and embryonic stem cells treated with ascorbic acid, respectively (Makino et al., (1999) J. Clin. Invest. 103(5), 697-705; and Takahashi et al., (2003) Circulation 107(14), 1912-1916). These results suggested that ascorbic acid was able to induce the differentiation of porcine MSCs into a myogenic lineage, including cardiomyocytes.

Figure 6:
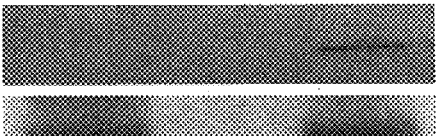
FIG. 6 illustrates the expression pattern of myogenic lineage markers of cardiac troponin I and connexin 43 analyzed by western blotting in fast growing MSCs clones treated with or without ascorbic acid.

FIG. 6 further confirmed the ascorbic acid-induced cardio differentiation of MSCs by the expression of a heart specific protein, i.e., cardiac troponin 1, in the fast growing BMSC clones (clone No. 1). In contrast, the level of cardiac troponin I or connexin43 in the non-treated cells and/or non-myotube forming cells, was undetectable.

INDUSTRIAL APPLICABILITY

It is an advantage of the present invention that it provides an improved method of producing cardiomyocytes, which is simple, safe and easy to use, with cardiomyocytes producing rate between 20% to 35%, and preferably, 25%. It is still another advantage of this invention that the differentiated cardiomyocytes prepared according to the improved method of this invention are suitable as a cell sources for use in cell-based therapy for repairing damage heart tissue and/or heart tissue transplant.

The foregoing description of various embodiments of the invention has been presented for purpose of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of producing cardiomyocytes comprising the steps of selecting mammalian mesenchymal stem cell clones that have a doubling time of less than 25 hours and administering ascorbic acid as a sole differentiating agent to induce differentiation of the mesenchymal stem cells into cardiomyocytes.

2. The method of claim 1, wherein the amount of ascorbic acid is between 100 μM to 10 mM.

3. The method of claim 2, wherein the amount of ascorbic acid is about 1 mM.

* * * * *